(12) United States Patent
Huang

(10) Patent No.: US 7,510,733 B2
(45) Date of Patent: Mar. 31, 2009

(54) EPIMERDINOSIDE A ORAL PHARMACEUTICS CONTAINING THE SAME AND PREPARATORY AND DETERMINATION METHODS

(75) Inventor: Huan Huang, Shanghai (CN)

(73) Assignee: Shanghai Yao Gang Biological Technology Co., Ltd., Shanghai (CN)

( * ) Notice: Subject to any disclaimer, the term of this patent is extended or adjusted under 35 U.S.C. 154(b) by 80 days.

(21) Appl. No.: 10/572,559

(22) PCT Filed: Sep. 20, 2004

(86) PCT No.: PCT/CN2004/001070

§ 371 (c)(1),
(2), (4) Date: Mar. 17, 2006

(87) PCT Pub. No.: WO2005/028491

PCT Pub. Date: Mar. 31, 2005

(65) Prior Publication Data

US 2007/0031523 A1    Feb. 8, 2007

(30) Foreign Application Priority Data

Sep. 19, 2003 (CN) ................ 03 1 50997
Sep. 19, 2003 (CN) ................ 03 1 50998

(51) Int. Cl.
A61K 36/00    (2006.01)
A01N 37/00    (2006.01)
A01N 31/00    (2006.01)

(52) U.S. Cl. .................. 424/773; 424/725; 514/577; 514/738

(58) Field of Classification Search .................. None
See application file for complete search history.

(56) References Cited

OTHER PUBLICATIONS

Calis et al (Phytochemistry 23 (10): 2313-2315, 1984).*
Dharmasiri et al (Pharmaceutical Biology 40 (6): 433-439, 2002).*
Arisawa et al (Planta Medica 38-41, 1986).*

* cited by examiner

*Primary Examiner*—Christopher R. Tate
*Assistant Examiner*—Qiuwen Mi
(74) *Attorney, Agent, or Firm*—Rabin & Berdo, P.C.

(57) ABSTRACT

Epimeredinoside A extracted from *Epimeredi indica* root, oral pharmaceutics made up with the *Epimeredi indica* root extract and at least one pharmaceutical adjuvant, and preparatory method for the oral pharmaceutics. The root extract is the extracta sicca prepared by water extraction and concentration of *Epimeredi indica* root, and contains 0.10% to 1.50% of epimeredinoside A. The inventive pharmaceutics of *Epimeredi indica* root extract do not contain any hormone and progesterone is not needed to be taken to prevent a side effect after using the drug. The pharmaceutics has doubtless effect in treating female menopause.

5 Claims, 3 Drawing Sheets

Figure 1:
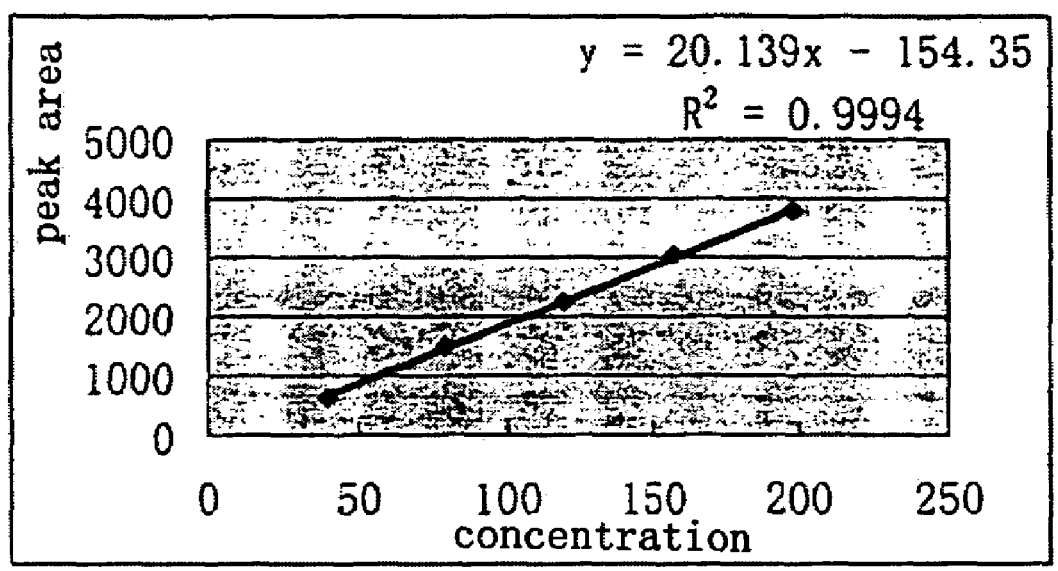

EPIMERDINOSIDE A ORAL PHARMACEUTICS CONTAINING THE SAME AND PREPARATORY AND DETERMINATION METHODS

BACKGROUND OF THE INVENTION

1. Field of the Invention

This invention relates to the field of TCM pharmaceutics, mainly dealing with anti-female menopausal-syndrome-effective epimeredinoside A, and epimeredinoside A-contained pharmaceutics of *Epimeredi indica* extract and the pharmaceutics' preparatory method.

2. Background of the Related Art

Estrogen and its pharmaceutics have been applied widely for the treatment of menopausal syndrome for a long time. However, it is hard to gain acceptance by women due to its many side effects and adverse reaction, even leading to cancer. Therefore, there is no satisfactory clinical drug at present.

*Epimeredi indica* (L.) Rothmalex, Guang-Fang-Feng, also named Fang-Feng-Cao, is recorded in *The Dictionary of Traditional Medicine* and is the whole plant of *Epimeredi indica* in the Labiatae family. It has been used in the treatment of many disorders such as cold with fever, disgorging, abdominal pain, bones and muscles pain, pyocutaneous disease, eczema, hemorrhoids and so on. It is used in the formula of Guanfang Ganmao Pills recorded in Volume 20 of Zhong-Yao-Cheng-Fang-Zhi-Ji (the TCM Pharmaceutics of Patent Formula) published by the Ministry of Public Health of the People's Republic of China.

A new use for *Epimeredi indica* root has been announced in Chinese Patent No. 02110522.7 by the inventor. *Epimeredi indica* root has the effects of ameliorating ovary function and regulating estrogen and progestogen, therefore it can be used to prepare drugs and health care products to treat and prevent many diseases due to the imbalance of estrogen and progestogen.

SUMMARY OF THE INVENTION

The present invention further develops pharmaceutics of *Epimeredi indica* root extract on the basis of Chinese Patent No. 02110522.7, about a novel oral pharmaceutics with clear active constituent and its content and stable quality.

The present invention announces all kinds of pharmaceutics related to any oral pharmaceutics composed of *Epimeredi indica* root extract and pharmaceutical adjuvant. This extract is obtained from extracts of *Epimeredi indica* root, after being extracted by water and concentrated by distillation, containing 0.10% to 1.50% of epimeredinoside A.

Pharmaceutical adjuvants involved in the present invention are all common adjuvants in regular pharmaceutics. The oral pharmaceutics are any oral dosage forms widely used in the medical area including hard capsule, soft capsule, granule, tablet, oral liquid and so on.

Another technical point announced in the present invention is the preparatory method of the extract and determination method of active constituents in it.

A preparatory method for *Epimeredi indica* root extracts of the present invention comprises the following steps:

1. The roots of *Epimeredi indica* were powdered. Then, a 10 times amount of water was added, and extraction conducted two times, for 1~2 hours per time. After filtration, it was concentrated as extracta sicca to a density of 1.01 to 1.08 (25~30° C.), then dried by spray or vacuum. The content of epimeredinoside A in this extract was 0.10 to 1.50% as determined by HPLC.

2. Proportions of extracts and adjuvants were mixed well to prepare various pharmaceutics conventionally by wet or dry granulation.

The content determination method of Epimeredinoside A in extracts of *Epimeredi indica* root of the present invention comprises the following steps of:

1. Apparatus and Materials:
   Instrument: Agilent 1100 HPLC system
   Standard: epimeredinoside A
   Chemical reagents: methanol, acetonitrile, distilled water and other reagents were HPLC grade
   Sample: Extracts of *Epimeredi indica* root (Shanghai Yaogang Biotechnology Ltd. Co.)

2. Chromatographic Conditions:
   Chromatographic column: Discovery $C_{18}$ (250 mm×4.6 mm, 5 μm)
   Mobile phase: acetonitrile:water=27:73
   Flow rate: 1.0 ml/min
   Column temperature: room temperature
   Detection wavelength: 320 nm
   Injection volume: 20 ul 3. Calibration Curve:
   Preparation of standard stock solutions: The standard was prepared by weighing 4.95 mg, and dissolving and diluting with methanol in a 25 ml volumetric flask to obtain standard stock solutions for the calibration curves.
   The Calibration Curves: From the stock solution, 0.4, 0.8, 1.2, 1.6, and 2.0 ml were weighed, respectively, dissolved, and diluted with methanol in 2 ml volumetric flasks to obtain standard solutions at concentrations of 39.6 μg/ml, 79.2 μg/ml, 118.8 μg/ml, 158.4 μg/ml, and 198 μg/ml, respectively.

A total of 20 μL of each standard solution was subjected to HPLC quantitative analysis. A calibration curve was generated to confirm the linear relationship between the peak area ratio (Y axis) and the concentrations of the standard (X axis) in the test samples. The calibration curves were found to be linear and could be described by the regression equations Y=20.139X−154.35, with coefficient $R^2$=0.9994. The range of calibration curves was 0.792-3.96 μg, and the retention time of epimeredinoside A was 9.55 min.

4. Sample Determination

Preparation of the standard solutions: The standard was accurately weighed, and dissolved and diluted with methanol in a volumetric flask to obtain standard solutions. A total of 20 μL of standard solution was subject to HPLC quantitative analysis and the peak area was recorded. The content of epimeredinoside A was calculated using the calibration curves accordingly, see FIG. 2.

Preparation of the sample solutions: The extracts of *Epimeredi indica* root (176.66 mg) were accurately weighted, and extracted by ultrasonication at room temperature for 2 times, then centrifuged. The supernatants were combined and diluted with water in a 10 ml volumetric flask. The solution was filtered through a syringe filter (0.45 μm).

The sample solutions were subjected to HPLC analysis as described above. The content of epimeredinoside A in the samples was calculated according to the calibration curves.

Formula for calculation is as follows:

$$Y=20.139X-154.35$$

Y: value of peak area
X: value of sample concentration (μg/ml)

The content of epimeredinoside A in a sample is demonstrated as X*10/*amount of sample*100%.

Figure 2:
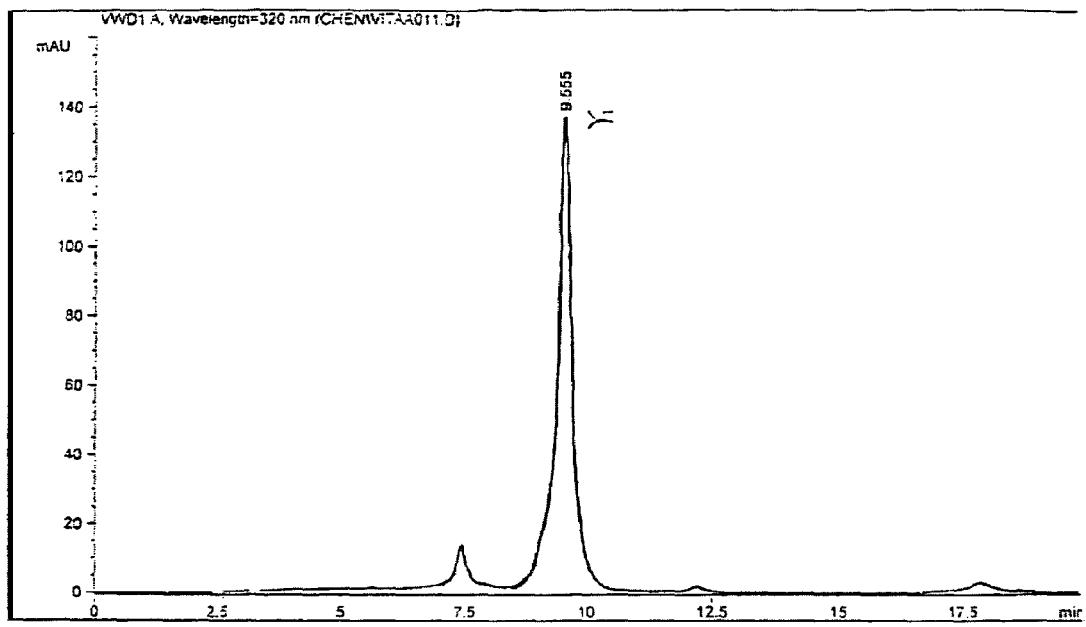

The Epimeredinoside A used in the present invention is an active compound obtained from extracts of *Epimeredi indica* root through isolation and purification. Extracts of *Epimeredi indica* root were extracted with n-butanol. The soluble extracts were then chromatographed on macroporous resin and a C-18 silicon column, eluted with ethanol gradient, collected and assayed by TLC. The ethanol elute was concentrated to obtain epimeredinoside A. FIG. 2 is its chromatogram of HPLC. Its structure is showed as follows:

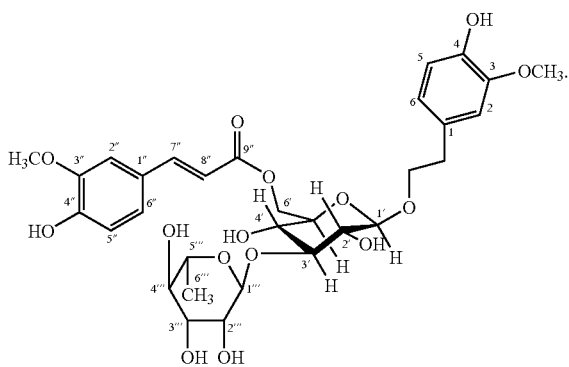

Validation of the HPLC methods for determination epimeredinoside A in the present invention:

(1) Calibration Curve:

Preparation of standard stock solutions: The standard was prepared by weighing 4.95 mg, and dissolving and diluting with methanol in a 25 ml volumetric flask to obtain standard stock solutions for the calibration curves.

The Calibration Curves: From the stock solutions, 0.4, 0.8, 1.2, 1.6, and 2.0 ml were weighed, respectively, dissolved, and diluted with methanol in 2 ml volumetric flasks to obtain standard solutions at concentrations of 39.6 µg/ml, 79.2 µg/ml, 118.8 µg/ml, 158.4 µg/ml, and 198 µg/ml, respectively.

A total of 20 µL of each standard solution was subjected to HPLC quantitative analysis. A calibration curve was generated to confirm the linear relationship between the peak area ratio (Y axis) and the concentrations of the standard (X axis) in the test samples. The calibration curves were found to be linear and could be described by the regression equations $Y=20.139X-154.35$, with coefficient $R^2=0.9994$. The range of calibration curves was 0.792-3.96 µg, and the retention time of epimeredinoside A was 9.55 min.

|  | Peak area | | | | |
|---|---|---|---|---|---|
|  | Number | | | | |
|  | 1 | 2 | 3 | 4 | 5 |
| Sample concentration (µg/ml) | 39.6 | 79.2 | 118.8 | 154.4 | 198 |
| Peak area (mAU) | 612.811 | 1472.17 | 2234.391 | 3036.277 | 3802.776 |

Calibration of epimeredinoside A is given in FIG. 1.

(2) Precision

To imbibe a standard solution at a concentration of 0.198 mg/ml for precision study under the above HPLC chromatographic conditions, then inject the above standard solution six times consecutively.

| Number | Peak area | X | RSD (%) |
|---|---|---|---|
| 1 | 3802.776 | 3815.223 | 0.824 |
| 2 | 3806.568 | | |
| 3 | 3879.024 | | |
| 4 | 3796.254 | | |
| 5 | 3802.456 | | |
| 6 | 3804.259 | | |

The results showed that the precision of this method is preferable.

(3) Stability

Peak area of standard solution was assayed at 0, 4, 8, 12 h with an injection volume of 20 ul per time.

|  | Number | | | |
|---|---|---|---|---|
|  | 1 | 2 | 3 | 4 |
| Peak area | 3785.21 | 3749.56 | 3802.54 | 3855.23 |
| Mean | | 3798.135 | | |
| RSD (%) | | 1.16 | | |

(4) Reproducibility

Five samples that have the same batch number were prepared for measurement according to the criteria of the sample assay procedure mentioned above.

Peak area of epimeredinoside A in a sample solution was assayed with an injection volume of 20 µl.

|  | Number | | | | |
|---|---|---|---|---|---|
|  | 1 | 2 | 3 | 4 | 5 |
| Peak area | 522.824 | 531.245 | 536.258 | 522.356 | 514.252 |
| Mean | | | 525.387 | | |
| RSD (%) | | | 1.63 | | |

(5) Recovery

The determined samples were weighed accurately and the standard epimeredinoside A solutions were added into the samples accordingly, and the content of epimeredinoside A in samples were determined under the same conditions as described above.

| NO. | Sample/µg | Added/µg | Analysis/µg | Recovery | Average | RSD(%) |
|---|---|---|---|---|---|---|
| 1 | 38.643 | 31.68 | 68.495 | 97.400 | 98.292 | 5.26 |
| 2 | 38.643 | 31.68 | 66.455 | 94.500 | | |
| 3 | 38.643 | 39.6 | 72.922 | 93.199 | | |
| 4 | 38.643 | 39.6 | 74.8 | 95.600 | | |
| 5 | 38.643 | 47.52 | 99.362 | 102.552 | | |
| 6 | 38.643 | 47.52 | 91.764 | 106.500 | | |

The results showed that a sensitive and stable analysis method for the determination of *Epimeredi indica* Root Extract was established.

The inventive pharmaceutics of *Epimeredi indica* Root Extract do not contain any hormone. No progesterone is needed to be taken to prevent a side effect after using the drug. It is compatible for a female in menopause that the drug has doubtless effect in clinic, stability, controllable and safety. Furthermore, a new approach was provided for patients which need to use estrogen but with contraindication of hormone.

BRIEF DESCRIPTION OF THE VARIOUS VIEWS OF THE DRAWING

Figure 3:
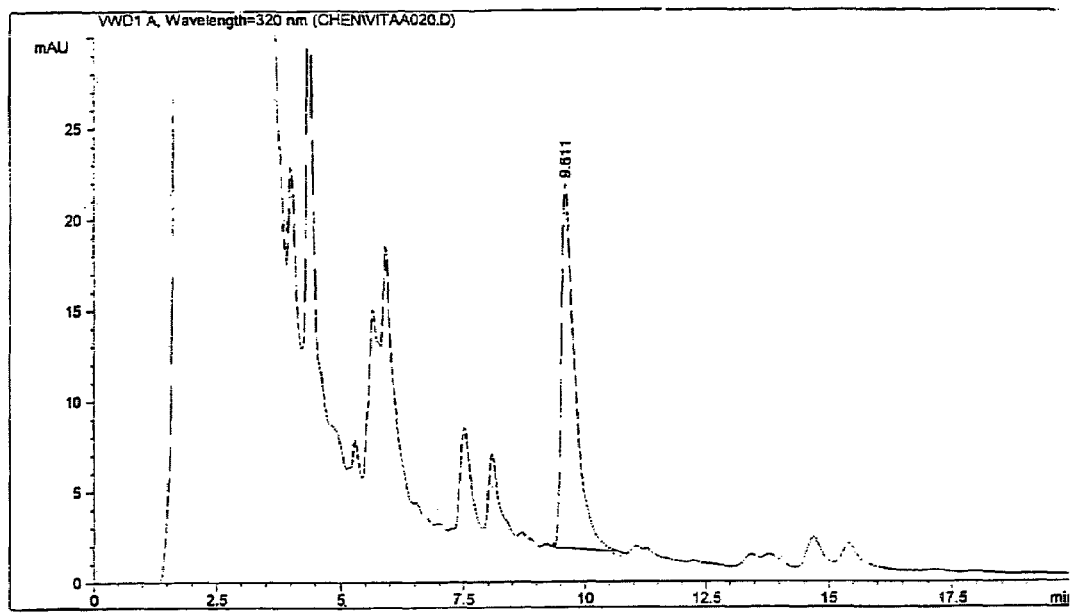

FIG. 1: Calibration curve of the epimeredinoside A;
FIG. 2: HPLC chromatogram of epimeredinoside A; and
FIG. 3: HPLC chromatogram of *Epimeredi indica* Root Extract.

DETAILED DESCRIPTION OF THE INVENTION

Example 1

Preparation of Epimeredinoside A (1) The dried and powdered root of *Epimeredi indica* was extracted with 10 fold water for 2 hours, and filtered. The residue was extracted with 8 fold water for 2 hours again, and filtered. The filtrates were combined and evaporated under vacuum to afford *Epimeredi indica* Root Extracts.

(2) The 6 kg of *Epimeredi indica* Root Extracts was extracted with 10 fold water for 3 times, and the solvent was evaporated to 600 ml. The residues were extracted with aqua-saturated n-butanol for 3 times (400 ml/time). The n-butanol solvent was evaporated under vacuum. The extracts of n-butanol were dissolved in water and chromatographed in a macroporous resin column (AB-8, Nankai Chemistry Factory, Tianjin). The chromatographic column was eluted with gradient mixtures of 20%, 50% and 95% aqueous ethanol successively. The elutes of 50% ethanol were concentrated and then dissolved with 50% aqueous methanol. The samples of 50% methanol were chromatographed on a RP-C18 silica column, eluted with 50% aqueous methanol to produce epimeredinoside A.

The structure of epimeredinoside A was elucidated by UV, IR, ESI, HRESI, NMR, 2D-NMR (COSY, HMQC, HMBC, NOESY) data. Epimeredinoside A, mp 139~142□, molecular formula of $C_{13}H_{40}O_{15}$ and the molecular weight 652, was isolated. The $^1$H NMR (500 MHz) and $^{13}$C NMR (125 MHz) spectral data of Epimeredinoside A (CDCl$_3$) was shown in Table 1.

TABLE 1

$^1$H NMR (500 MHz) and $^{13}$C NMR (125 MHz) spectral data of Epimeredinoside A (CDCl$_3$)

| Ferulic acid | δC | ΔH | Aglycone | ΔC | δH |
|---|---|---|---|---|---|
| 1 | 127.68 | | 1 | 132.69 | |
| 2 | 111.66 | 7.15(d, 2) | 2 | 117.00 | 6.69(d, 2) |
| 3 | 150.64 | | 3 | 147.47 | |
| 4 | 149.36 | | 4 | 147.33 | |
| 5 | 116.47 | 6.80(d, 8) | 5 | 112.81 | 6.65(d, 8) |
| 6 | 124.27 | 7.02(dd, 8, 2) | 6 | 121.11 | 6.61(dd, 8, 2) |
| 7 | 147.10 | 7.62(d, 16) | α | 36.71 | 2.80(t, 7) |
| 8 | 115.28 | 6.39(d, 16) | β | 72.31 | 3.5-4.2 |
| 9 | 169.07 | | OCH3 | 55.40 | 3.76(s) |
| OCH3 | 55.44 | 3.86(s) | | | |

| Glucose | δC | ΔH | Rhamnose | ΔC | δH |
|---|---|---|---|---|---|
| 1 | 104.39 | 4.33(d, 8) | 1 | 102.73 | 5.18(d, 1) |
| 2 | 75.66 | 3.5-4.2 | 2 | 72.34 | 3.5-4.2 |
| 3 | 84.08 | 3.53(m) | 3 | 72.25 | 3.5-4.2 |
| 4 | 70.54 | 3.5-4.2 | 4 | 73.99 | 3.5-4.2 |
| 5 | 75.37 | 3.5-4.2 | 5 | 70.05 | 3.5-4.2 |
| 6 | 64.48 | 4.41(m) | 6 | 17.88 | 1.25(d, 6) |

Example 2

Preparation and Quantitative Analysis of *Epimeredi indica* Root Extract

A: The dried and powdered root of *Epimeredi indica* was extracted with 10 fold water, and filtered. The residue was extracted with 8 fold water for 2 hours again, and filtered. The filtrates were combined and concentrated under vacuum to obtain the extracts of *Epimeredi indica* Root.

B: Quantitative Analysis

1. Apparatus and Materials

Apparatus: Agilent 1100 HPLC system.
Standard: Epimeredinoside A
Chemical reagents: Methanol, acetonitrile, water and other chemical reagents were HPLC-grade.
Samples: Extracts of *Epimeredi indica* Root (Shanghai Yaogang Biotech Co. Ltd)

2. Chromatographic Conditions

Column: Discovery C18 (250 mm×4.6 mm, 5 μm)
Mobile phase: Acetonitrile:Water=27:73
Flow rate: 1.0 ml/min
Column temperature: Room temperature
Detector wavelength: 320 nm
Injection volume: 20 μl 3. Calibration Curves Preparation of standard stock solutions: The standard was prepared by weighing 4.95 mg, and dissolving and diluting with methanol in a 25 ml volumetric flask to obtain standard stock solutions for the calibration curves.

The Calibration Curves: From the stock solutions 0.4, 0.8, 1.2, 1.6, and 2.0 ml were weighed, dissolved, and diluted with methanol in 2 ml volumetric flask to obtain standard solutions at concentrations of 39.6 μg/ml, 79.2 μg/ml, 118.8 μg/ml, 158.4 μg/ml, and 198 μg/ml, respectively. A total of 20 μL of each standard solution was subject to HPLC quantitative analysis. A calibration curve was generated to confirm the linear relationship between the peak area ratio (Y axis) and the concentrations of the standard (X axis) in the test samples. The calibration curves were found to be linear and could be described by the regression equations Y=20.139X−154.35, with coefficient $R^2$=0.9994. The range of calibration curves was 0.792-3.96 μg, and the retention time of epimeredinoside A was 9.55 min.

4. Samples Analysis

Preparation of the standard solutions: The standard was accurately weighed, dissolved, and diluted with methanol in a volumetric flask to obtain standard solutions. A total of 20 μL of standard solution was subject to HPLC quantitative analysis and the peak area was recorded. The contents of epimeredinoside A was calculated using the calibration curves accordingly, see FIG. 2.

Preparation of the sample solutions: The extracts of *Epimeredi indica* root (176.66 mg) were accurately weighted, and extracted with by ultrasonication at room temperature for 2 times, then centrifuged. The supernatants were combined and diluted with water in a 10 ml volumetric flask. The solution was filtered through a syringe filter (0.45 μm).

The sample solutions were subjected to HPLC analysis as described above, shown in FIG. 3

The content of epimeredinoside A in samples were calculated according to the calibration curves.

Peak area (Y): 383.380.

The concentration X is 26.70 μg/ml according to the regression equations Y=20.139X−154.35.

The content of epimeredinoside A in the sample was 0.15% by the equation X*10/Sample Amount*100%.

Example 3

Preparation of a Granulate

Formula:

| Extracts of *Epimeredi indica* Root | 150 g |
| Lactose | 50 g |
| Stearate Magnesium | 2 g |

Methods: The extracts of *Epimeredi indica* Root which were prepared as described in Example 2 were mixed with lactose and stearate magnesium, and then sieved. The granulate was obtained by sieving again. The content of epimeredinoside A was 0.17%.

Example 4

Preparation of a Granulate

Formula:

| Extracts of the *Epimeredi indica* Root | 130 g |
| Lactose | 70 g |
| Stearate Magnesium | 1 g |

Methods: The extracts of *Epimeredi indica* Root which were prepared as described in Example 2 were mixed with lactose and stearate magnesium, and then sieved. The granulate was obtained by sieving again. The content of epimeredinoside A was 0.13%.

Example 5

Preparation of a Capsule

Formula:

| Extracts *Epimeredi indica* Root | 110 g |
| Lactose | 90 g |
| Stearate Magnesium | 1 g |

Methods: The extracts of *Epimeredi indica* Root which were prepared as described in Example 2 were mixed with lactose and stearate magnesium, and then sieved. The grain was sieved again. The capsules were filled with the fine grain.

The content of epimeredinoside A was 0.27%.

Example 6

Preparation of a Tablet

Formula:

| The extracts of *Epimeredi indica* Root | 230 g |
| Cellulose, Microcrystalline | 20 g |
| Carboxymethyl starch sodium | 3 g |
| Polyvinylpyrrolidone | 1 g |
| Pulvis Talci | 1 g |
| Stearate Magnesium | 1 g |

Methods: The Microcrystalline Cellulose, Sodium Carboxymethyl Starch and other materials were mixed in a mortar, and the extracts of *Epimeredi indica* Root which were prepared as described in Example 2 were added. The powder was shaped in a muller. The fine powder was granulated, dried and Magnesium Stearate added. The granulate was tableted and coated. The content of epimeredinoside A was 0.23%.

Example 7

Preparation of a Tablet

Formula:

| The extracts of *Epimeredi indica* Root | 300 g |
| Cellulose, Microcrystalline | 26 g |
| Carboxymethyl starch sodium | 2.8 g |
| Polyvinylpyrrolidone | 2.8 g |
| Pulvis Talci | 2.8 g |
| Stearate Magnesium | 1 g |

Preparation was carried out according to the method mentioned in Example 6. The concentration of epimeredinoside A was 0.22%.

The invention claimed is:

1. An isolated compound named epimeredinoside A having formula I as follows:

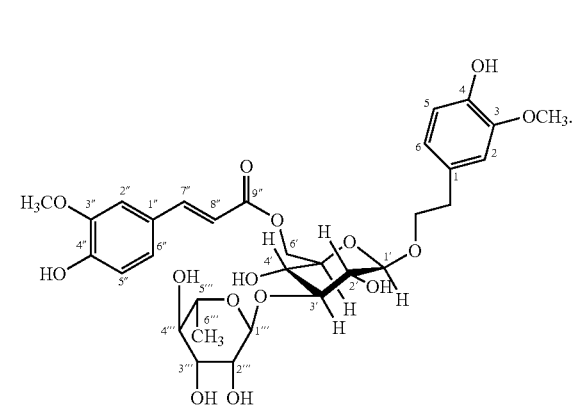

2. An oral pharmaceutical composition comprising an *Epimeredi indica* root extract containing from 0.10 to 1.50% by weight of epimeredinoside A, wherein the extract has been obtained by extracting *Epimeredi indica* root with water and concentrating by distillation; and at least one pharmaceutical adjuvant.

3. The oral pharmaceutical composition according to claim 2, wherein the composition is an oral form selected from the group consisting of hard capsule, soft capsule, granule, tablet, and oral liquid.

4. A preparation method for preparing oral pharmaceutics from *Epimeredi indica* root extract, comprising:

making a powder of *Epimeredi indica* roots;

adding water to the powder in an amount of about 10 times that of the powder and extracting for a time ranging from 1 to 2 hours;

filtering to obtain a first filtrate and a first cake;

adding water to the first cake in an amount of about 10 times that of the first cake and extracting for a time ranging from 1 to 2 hours;

filtering to obtain a second filtrate and a second cake;

combining the first filtrate and the second filtrate to provide a combined filtrate;

concentrating the combined filtrate as extracta sicca to a density ranging from 1.01 to 1.08 and a content of epimeredinoside A ranging from 0.10 to 1.50% as determined by HPLC;

drying the extracta sicca by spray or vacuum; and mixing predetermined quantities of the dried extract and at least one adjuvant.

5. The preparation method according claim 4, wherein the content of epimeredinoside A in the dried extract of *Epimeredi indica* root is determined by HPLC, which comprises the steps of:

a. providing (1) an HPLC apparatus, (2) a Standard sample of epimeredinoside A, (3) HPLC grade chemical reagents including methanol, acetonitrile, and distilled water, and (4) extracts of *Epimeredi indica* root;

b. operating the HPLC apparatus under conditions including (1) using a Chromatographic column: Discovery $C_{18}$ (250 mm×4.6 mm, 5 μm), (2) using a mobile phase which is a mixture of acetonitrile and water having an acetonitrile: water ratio of 27:73, (3) using a flow rate of 1.0 ml/min, (4) using a column temperature which is room temperature, and (5) using a detection wavelength of 320 nm, and (6) using an injection volume of 20 μl;

c. generating a calibration curve by (1) preparing standard solutions of epimeredinoside A having respective concentrations of 39.6 μg/ml, 79.2 μg/ml, 118.8 μg/ml, 158.4 μg/ml, and 198 μg/ml; (2) subjecting each standard solution to HPLC quantitative analysis; (3) generating a calibration curve to confirm a linear relationship between peak area ratio (Y axis) and the concentrations of the standard solutions (X axis);

d. preparing test samples; and e. subjecting the test samples to the HPLC quantitative analysis;

f. determining the content of epimeredinoside A in the test samples from the calibration curves using, as a formula for calculation, Y=20.139X−154.35, where Y is peak area and X is sample concentration (μg/ml).

* * * * *